United States Patent [19]

Devereux

[11] Patent Number: 4,655,221
[45] Date of Patent: Apr. 7, 1987

[54] METHOD OF USING A SURGICAL REPAIR MESH

[75] Inventor: Dennis F. Devereux, Pennington, N.J.

[73] Assignee: American Cyanamid Company, Stamford, Conn.

[21] Appl. No.: 731,198

[22] Filed: May 6, 1985

[51] Int. Cl.⁴ .............................................. A61B 17/04
[52] U.S. Cl. ................................................. 128/334 R
[58] Field of Search ................. 128/334 R, 335.5, 1 R; 3/12; 604/364

[56] References Cited

U.S. PATENT DOCUMENTS

| 3,124,136 | 3/1964 | Usher | 128/334 R |
| 3,875,937 | 4/1975 | Schmitt et al. | 128/334 R |
| 4,347,847 | 9/1982 | Usher | 128/334 R |
| 4,429,080 | 1/1984 | Casey et al. | 128/334 R |
| 4,520,821 | 6/1985 | Schmidt et al. | 128/334 R |
| 4,546,152 | 10/1985 | Koelmel et al. | 128/334 R |

FOREIGN PATENT DOCUMENTS 60-14861  1/1985  Japan .

OTHER PUBLICATIONS

"Small Bowel Exclusion . . . by a Polyglycolic Acid Mesh Sling" D. F. Devereux, M.D. et al., J. of Surgical Oncology 26 107-112 (Jun. 1984).

Primary Examiner—John D. Yasko
Attorney, Agent, or Firm—Charles F. Costello, Jr.

[57] ABSTRACT

A polyglycolic acid mesh sling sewn above the pelvic inlet prevents small bowel descent into the true pelvis during radiation therapy for various pelvic malignancies.

19 Claims, 7 Drawing Figures

METHOD OF USING A SURGICAL REPAIR MESH

BACKGROUND OF THE INVENTION

This invention relates to the use of a polyglycolic acid mesh sling. The sling is sewn, e.g., above the pelvic inlet. The method prevents the small bowel descent into the true pelvis. The invention is useful during radiation therapy, e.g. for various pelvic malignancies.

Colorectal carcinoma is the commonest malignancy affecting both males and females in the United States. The American Cancer Society has predicted that approximately 59,000 Americans will die from the disease in 1983. The rectal component is particularly worrisome because of its high incidence of local regional recurrence. Radiation therapy in these cases is limited to 4,500 cGy. This limitation is based on the fear of inducing small bowel enteritis and arteritis (irreversible damage).

Radiation enteritis is also a complication seen in patients receiving irradiation therapy, e.g., for perineal, pelvic, or intra-abdominal malignancies. It is difficult to obtain an accurate incidence but an estimate is that it occurs in about 5% of patients undergoing irradiation for various malignancies. See e.g., Morgenstern L., Thompson R., and Friedman N.: The Modern Enigma of Radiation Enteropathy: Sequelae and Solutions. Am J Surg. 134: 166–172. 1977. Small bowel obstruction has been noted to double from 5%, with a surgical operation alone, to 12% when surgery is combined with postoperative radiation therapy. Risk factors of previous surgery, diabetes, and hypertension are also known to increase the incidence of radiation-associated small bowel injury. There has been no significant advance made in managing or preventing radiation-induced enteropathy over the last few decades.

Prior attempts to solve this problem have included various chemical treatments. Special diets have also been studied in an attempt to reduce radiation enteropathy. See, e.g. Donaldson S., Jundt S., Ricour C., et al: Radiation Enteritis in Children: A Retrospective Review, Clinicopathologic Correlation, and Dietary Management, CANCER 35: 1167, 1975. Radiation enteropathy may occur when the total dose exceeds 4,500 rads or greater. These prior art attempts are experimental. That is, they have no proven clinical benefit.

There is a relatively large incidence of pelvic and perineal recurrence seen in patients with Dukes pathological stage B2, C1, and C2 rectal lesions. The patients are irradiated preoperatively, postoperatively, or by the "sandwich" technique in attempts to control local recurrence. Many of the patients are treated surgically by either low anterior or abdominoperineal resection. This allows the small bowel to descend below the former peritoneal floor postoperatively and it is therefore at risk for radiation-associated injury.

A surgical mesh material, described e.g. in U.S. Ser. No. 606,104 filed Apr. 26, 1984 and entitled "Surgical Rapair Mesh", when used with the surgical procedure of this invention, prevents small bowel descent below the true pelvic inlet and into the true pelvis. The true pelvic inlet is on a line drawn between the sacral promentory and the pubic ramus. The surgical procedure is used after low anterior resection, hysterectomy or abdominoperineal resection. The procedure is also useful in patients with pelvic malignancies. It may also be useful for patients with the need for adjuvant radiotherapy or in those with known pelvic recurrences requiring radiation therapy as part of their management.

This invention is concerned with a textile material which may be either knit or woven. The material can be made from a tissue absorbable material such as polyglycolic acid (herein PGA) fibers. It is to be understood that the term polyglycolic acid is generic to both the homopolymer and to copolymers containing a glycolic acid ester linkage.

The textile material can be a mesh or fabric which has varying amounts of stretch, including zero stretch in the warp or in the weft (filling) direction.

Although the dimensions and weight of the mesh are only limited by the practical size for its intended use, dimensions of from 4×4 inches to 10×13 inches and weights of 0.75 to 6.5 ounces per square yard can be normally used. Openings in the mesh can range normally from zero to ¼ inch.

In order to further stabilize the textile material, that is to eliminate horizontal or vertical edge curling and regulate stretch, the material may be heat set by holding both length and width to a specified dimension within a pin or clip frame while exposing it to temperatures of 90° to 175° C. for periods of 30 seconds to 15 minutes, preferably in a vacuum. The material may also be heat set by holding both the length and width to a specified dimension on a heated cylinder while exposing it to temperatures of 90° to 175° C. for periods of up to 4 hours in a vacuum.

The use of the above-described surgical mesh reduces radiation associated small bowel injury, which is a chronic, unrelenting, clinical problem.

This invention provides for the surgical placement of a polyglycolic acid (which may hereafter be abbreviated as PGA) mesh sling to exclude the small bowel from the true pelvis. The invention may allow higher doses of radiation therapy to be delivered to the area of concern in patients at high risk for, or with actual local recurrence of, pelvic malignancies. The technique appears safe and is free of foreign-body sepsis due to the resorbtive qualities of the PGA. At this time, the surgical procedure is not associated with small bowel obstruction or injury.

The technique can be used in all patients at high risk for local recurrence due to pelvic or rectal malignancies in an attempt to achieve better local postoperative control with adjunctive radiation therapy.

This new use for the PGA Mesh solves an old problem for surgeons, namely: how do we prevent small bowel descent into the pelvis after pelvic surgery? Small bowel descent is the limiting factor to postoperative X-Ray therapy (XRT). Use of the PGA mesh enables us to give postoperative XRT without damage to the small bowel.

The problem of radiation enteritis has been solved by the method of using PGA mesh with this invention. Specifically, the method has solved the following questions:

1. Is a PGA mesh capable of keeping the small bowel out of the pelvis?
2. Is a PGA mesh associated with small bowel obstruction?
3. Is a PGA mesh associated with a reduction in GI transit time?

SUMMARY OF THE INVENTION

A surgical method of using a material manufactured from a bioabsorbable polymer on a warm blooded mammal has been invented. The method comprises opening the abdomen of said mammal; elevating at least one pelvic organ essentially above the true pelvic inlet; attaching the material around the peritoneal cavity; and closing said abdomen.

In one embodiment, the material is a textile material. In another embodiment, the pelvic organ is selected from the group consisting of the small bowel, liver, spleen, and stomach. In a specific embodiment, the pelvic organ is the small bowel.

In still another embodiment, the method comprises elevating at least the small bowel, liver, spleen and stomach out of the pelvis. In yet another embodiment, the method comprises suturing the material around the peritoneal cavity. In a further embodiment, the method comprises stapling the material around the peritoneal cavity.

A method of using a knitted surgical material on a warm-blooded mammal has also been invented. The material comprises a plurality of filaments. Each filament is manufactured from a polymer having a glycolic acid ester linkage. The filaments are bundled or twisted into a yarn. The yarn is knitted into a surgical material. The method comprises opening of the abdomen of the mammal; elevating at least one pelvic organ essentially out of the true pelvis; attaching the material around the peritoneal cavity; and closing the abdomen.

In one embodiment, the knitted material is a mesh. In another embodiment, the material is a fabric.

In still another embodiment, the polymer is a homopolymer. In yet another embodiment, the polymer is a copolymer. In a specific embodiment, the yarn is greater than about 60 denier and contains up to 4 plys, each ply having greater than about 25 filaments. In a more specific embodiment, the yarn is up to about 150 denier and contains up to about 75 filaments. In a still more specific embodiment, the yarn is about 100 to 135 denier and contains about 40 to 75 filaments.

The above embodiments can be manufactured on a 48 gauge Raschel knitting machine wherein the stitch design is Front Bar: 1/0 0/1, and
Back Bar: 1/0 4/5.

In yet another embodiment, the weight of the fabric is about 4 to 10 oz./sq. yd. In a further embodiment the quality of the fabric is about 10 to 20 inches per 480 courses.

An alternative method of using a knitted surgical mesh on a warm blooded mammal has also been invented. The mesh comprises a plurality of filaments. Each filament is manufactured from a polymer having a glycolic acid ester linkage. The filaments are bundled or twisted into a yarn. The yarn is knitted into a mesh.

The alternative method comprises opening the abdomen of a mammal; elevating at least the small bowel essentially out of the true pelvis; placing the mesh adjacent to the intra-abdominal wall; suturing the mesh around the pertioneal cavity; and closing the abdomen.

DESCRIPTION OF THE INVENTION

Figure 1:
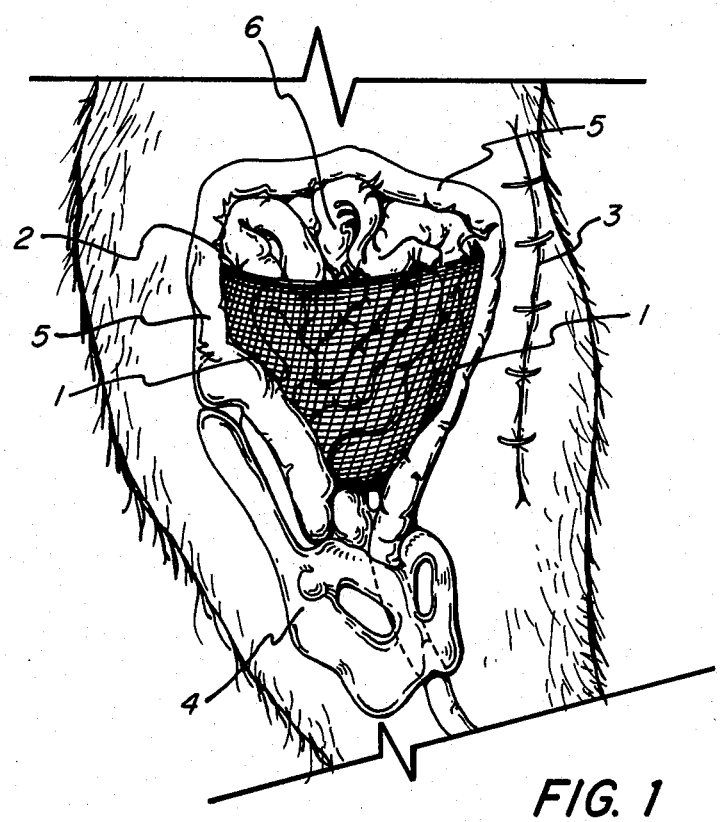
FIG. 1 is a schematic view showing the position of the surgical mesh to the elevated small bowel.
Figure 2:
FIGS. 2 and 3 are X-Ray photographs showing the upper abdominal position of the elevated small bowel.
Figure 3:

The abdomen is opened. A pelvic procedure e.g., a gynecologic, urologic or gastrointestinal procedure, is performed upon a pelvic organ. A PGA mesh, e.g. a mesh #2, which is commercially available from Davis & Geck, Danbury, Conn. 06810 U.S.A., is sewn in a circumferential manner around the inside of the peritoneal cavity. This elevates the small bowel out of the pelvis and away from the operated organs, as shown in FIGS. 1 to 3. Specifically, FIG. 1 shows a PGA mesh sling excluding the small bowel from the pelvic inlet of a mammal. FIG. 2 shows the upper abdominal position of the small bowel, thirty days postoperatively. FIG. 3 shows the upper abdominal position of the small bowel, ninety days postoperatively. In FIG. 3, the PGA mesh has been reabsorbed.

The novelty of the technique resides in its ability to prevent small bowel descent into the pelvis. This technique prevents any radiation damage to the small bowel in patients requiring it postoperatively.

Figure 4A:
FIGS. 4A and B are contrasting X-Ray photographs showing the presence and resorption of the mesh at 30 and 60 days respectively.
Figure 4B:

FIG. 4A is a cross-section of an abdominal wall of a mammal showing the presence of PGA mesh fibers at 30 days. FIG. 4B is a cross-section of an abdominal wall of a mammal at 60 days, showing the resorption process of PGA mesh fibers.

Figure 6:
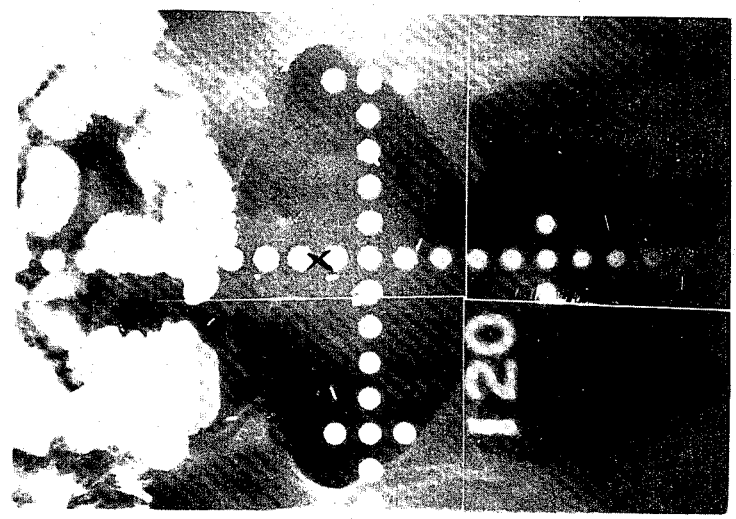
FIGS. 5 and 6 are X-Ray photographs of a simulated study showing the respective location of the small bowel before and after placement of the mesh sling.
Figure 5:
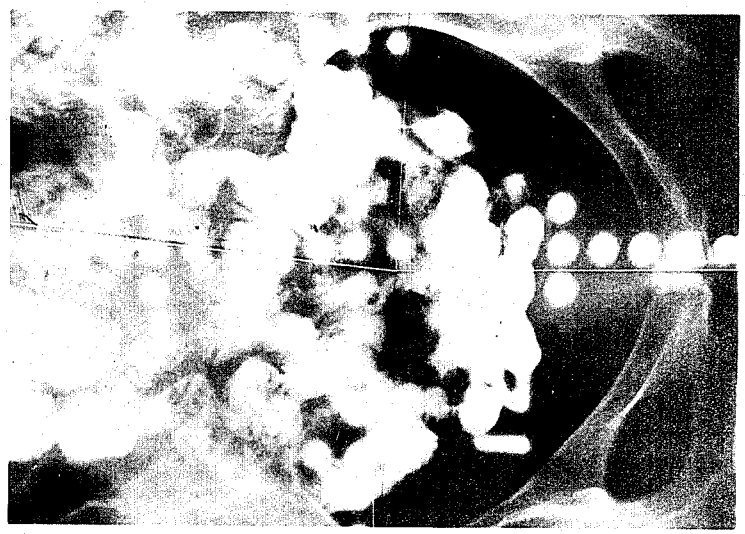

FIGS. 6 and 7 are simulation studies of a patient before and after placement of the polyglycolic acid mesh sling. These figures demonstrate small bowel exclusion from the true pelvis (the true pelvis is below a plane which intersects a line drawn between the sacral promentory and the pubic ramus). Specifically, FIG. 5 shows the small bowel residing in the pelvis, prior to sling placement. FIG. 6 shows the position of the small bowel three months after placement of the sling.

A discussion of FIGS. 1 to 6 is also described in Devereux, D. F., M.D., et al.: Small Bowel Exclusion From the Pelvis by a Polyglycolic Acid Mesh Sling, J. of Surgical Oncology 26: 107–112 (1984), which is incorporated herein by reference.

The term PGA is intended to be generic and means any polymer containing a glycolic acid ester linkage, that is, both a homopolymer and a copolymer.

ILLUSTRATIVE EMBODIMENT

The following technique can be used with essentially any warm blooded mammal. Referring to FIG. 1, a 7×9 PGA mesh 1 #2 is attached to the posterior intraabdominal wall superficial to the aorta and over the vertebral column. Two #2 PGA sutures 2 are used, each is used to secure "bites" 1 to 2 cm apart, in a locking fashion. One suture goes to the left of the mid-line and one to the right. They then both meet at the incision 3. This then forms a new peritoneal floor above the true pelvis 4. Also above the new peritoneal floor is the ascending and transverse colon 5 and the small intestine 6, and also the liver, spleen and stomach.

EXAMPLE 1

Twenty male Fischer rats weighing about 350 to 400 gm were placed on a D5 water per os (po) diet for 5 days preoperatively to promote a mechanical "bowel prep."

After 5 days they were ether-anesthetized, had a midline incision made, and had division of their rectum below the pelvic floor. The bowel was reanastomosed with a single layer of a 4-0 silk suture. The floor was not reperitonealized.

Ten animals had placement of a polyglycolic acid mesh sling from the retroperitoneum to the anterior abdominal wall, which contained all of the small bowel as shown in FIGS. 1 to 3. Ten other animals, as controls, did not have mesh placed or any other preventive measures taken to exclude the small bowel from entering the true pelvis postoperatively. Prophylactic antibiotics were not used.

Posterolaterally, a small "V" was fashioned in the polyglycolic mesh sling to allow passage of the ascending and descending colon. Abdominal wounds were closed in layers with a 3-0 silk suture. Animals were then allowed rat chow and water ad lib.

At 30, 60, 90 and 120 days postoperatively, randomly selected animals were anesthetized and had a soft silastic 16-gauge tube passed po and had 3.0 cc of barium injected into the stomach. The tube was then removed and anesthesia maintained.

At 15, 30 and 60 minutes thereafter and X-Ray was taken with the animal in the upright position to demonstrate the location of the small bowel in relation to the pelvic inlet. Animals were then sacrificed and the polyglycolic acid mesh sling in the abdominal cavity was photographed and sectioned for histological examination.

EXAMPLE 2

A number 2 polyglycolic acid mesh is placed in the abdominal cavity of two baboons and sewn circumferentially on the inside of the pertioneal cavity to keep the small bowel out of the true pelvis.

The mesh is sewn in a circumferential fashion over all retroperitoneal tissues with about 1 to 2 cm between stitches. The mesh is sewn with a locking PGA suture to the posterior (intraabdominal) wall over the vena cava, psoas muscles and if necessary, over the descending colon, up the lateral abdominal walls to the anterior (posterior rectus sheath) intraabdominal wall. This supports the small bowel and prevents its descent into the pelvis following surgery.

Transit time of the gastrointestinal (GI) tract for pre-mesh placement and 3 months after mesh placement was determined. The animals were sacrificed in six months for resection of the small bowel and biopsy in the areas to rule out obstructive phenomena.

RESULTS

In Examples 1 and 2 no animal who had placement of a PGA mesh sling developed a wound or mesh infection. No animal developed small bowel obstruction. The technique of mesh placement prevented small bowel descent into the true pelvis in all animals as shown in FIG. 2. No animal failed to keep the small bowel out of the true pelvis even after the polyglycolic acid mesh was resorbed as shown in FIG. 3.

Absorption of the mesh was complete by 60 days as shown in FIG. 5. At 120 days after surgery, the small bowel still remains fixed in the upper abdominal position.

Animals that were operated on but that had no mesh placed all had the small bowel identifiable around the point of anastomosis, which was obviously below the level of the true pelvis and obturator foramen.

The textile material used in this invention can be either a knitted or a woven fabric. The fabric can be of a medium weight.

One textile material which may be used in this invention is described more fully in Example 3. It is a stretchable knit mesh. The mesh can be manufactured on a 14 gauge tricot machine, or alternatively on a 28 gauge Raschel warp knit machine using a 2-bar construction. On either of these machines, the mesh is not heat set.

The yarn used in knitting the mesh can be between about 150 to 600 denier with between 1 and 5 turns per inch of twist. Preferably, the mesh has a lock stitch construction for nonravelling.

Another fabric which may be used in this invention is described in Examples 4 and 5. It is a semistretchable knit mesh. It can be knit on a 28 gauge tricot machine using a 1-bar construction. The mesh can be knit from a yarn having about 30 to 100 denier.

Another fabric is described more fully in Examples 6 and 7. It is also a knit fabric. The fabric is heat set without stretching, and is stabilized. The heat set can be on a tenter frame. The fabric can be manufactured on a 24 gauge tricot or 48 gauge Raschel machine using a 2-bar construction.

The fabric can be between about 75 to 250 denier with between about ¼ to 5 turns per inch. Preferably, the fabric is also manufactured using a chain stitch for stability.

Still another fabric is described in Examples 8 & 9. This fabric is a weave. The weave is stabilized. The fabric is manufactured on a loom.

The product is made from yarns of between about 150 to 350 denier. The warp yarn has between about 4 to 10 turns per inch of twist and the weft yarn has between about ¼ to 5 turns per inch of twist. The weave can be plain or it can have other configurations, e.g. twill or satin. Finally, the woven fabric has a water porosity of about zero to 1000 ml/min/cm$^2$ at 120 mm of mercury.

Examples of typical textile materials as contemplated as being useful with this invention are given below:

EXAMPLE 3

14 Gauge Tricot (14 Needles/Inch)

This example is a knitted mesh which has been neither stretched nor heat set.

(A) Stitch Design:
  Front bar: (2/0 2/4)×2, (4/6 4/2)×2
  Back bar: (4/6 4/2)×2, (2/0 2/4)×2
(B) Yarn description:
  3 ply 110 den./50 fil. of polyglycolic acid (homopolymer)
(C) Fabric Weight:
  5.0 to 7.5 oz./sq. yd.
(D) Fabric Quality:
  16 inches (per 480 courses)

EXAMPLE 4

28 Gauge Tricot (28 Needles/Inch)

This homopolymer example of a prior art glycolide and lactide copolymer tight knitted mesh has been both stretched and heat set. Further the knitted mesh has been prestressed, i.e., stretched prior to heat setting.

(A) Stitch Design:
  Front bar: 1/0 1/2
  Back bar: none
(B) Yarn description:

62 den./28 fil. of polyglycolic acid (homopolymer)
(C) Fabric weight:
  1.00 to 2.75 oz./sq. yd.
(D) Fabric quality:
  8 inches (per 480 courses)

EXAMPLE 5

28 Gauge Tricot (28 Needles/Inch)

This glycolide and trimethylene carbonate copolymer example of a prior art glycolide and lactide copolymer tight knitted mesh has been both stretched and heat set. The stitch design is the same as Example 2. Further, the knitted mesh has been prestressed, i.e., stretched prior to heat setting.
(A) Stitch design:
  Front bar: 1/0 1/2
  Back bar: none
(B) Yarn description:
  75 den./12 fil. of a glycolide and trimethylene carbonate copolymer.
(C) Fabric weight:
  1.00 to 2.75 oz./sq. yd.
(D) Fabric quality:
  8 inches (per 480 courses)

EXAMPLE 6

48 Gauge Raschel or 24 Gauge Tricot (24 Needles/Inch)

This example describes a knitted fabric which has been heat set but not stretched.
(A) Stitch design:
  Front bar: 1/0 0/1 (chain stitch)
  Back bar: 1/0 4/5
(B) Yarn description:
  123 den./56 fil. of polyglycolic acid (homopolymer)
(C) Fabric weight:
  6.25±0.50 oz./sq. yd.
(D) Fabric quality:
  14 inches (per 480 courses)

EXAMPLE 7

48 Gauge Raschel or 24 Gauge Tricot (24 Needles/Inch)

This example describes a knitted fabric which has been heat set but not stretched. The stitch design is the same as Example 4.
(A) Stitch design:
  Front bar: 1/0 0/1 (chain stitch)
  Back bar: 1/0 4/5
(B) Yarn description:
  110 den./50 fil. of polyglycolic acid (homopolymer)
(C) Fabric weight:
  5.85±0.60 oz./sq. yd.
(D) Fabric quality:
  14 inches (per 480 courses)

EXAMPLE 8

1×1 Plain Woven Fabric

This example teaches a woven fabric which has been neither stretched nor heat set.
(A) Warp yarn and filling yarns: 5 ply 46 denier/21 fil. of polyglycolic acid (homopolymer)
(B) Warp yarn twist: 5 turns per inch
(C) Filling yarn twist: 1.5 turns per inch
(D) Fabric weight: 4.00±0.50 oz./sq. yd.

EXAMPLE 9

1×1 Plain Woven Fabric

This example teaches a woven fabric which has been neither stretched nor heat set.
(A) Warp yarn and filling yarns: 250 denier/50 fil. of a glycolide and trimethylene carbonate copolymer.
(B) Warp yarn twist: 5 twists per inch
(C) Filling yarn twist: 1.5 twists per inch
(D) Fabric weight: 4.00±0.50 oz./sq. yd.

What is claimed is:

1. A surgical method of using a material manufactured from a bioabsorbable polymer in a warm-blooded mammal comprising:
  opening the abdomen of said mammal;
  elevating at least one pelvic organ essentially above the true pelvic inlet;
  placing the material beneath the organ or organs from the elevating step;
  attaching said material to the wall of the peritoneal cavity, thereby preventing said organ or organs from descending into said pelvic inlet; and
  closing said abdomen.

2. A method of claim 1 wherein said material is a textile material.

3. A method of claim 1 wherein said pelvic organ is selected from the group consisting of the small bowel, liver, spleen, and stomach.

4. A method of claim 3 wherein the pelvic organ is the small bowel.

5. A method of claim 1 comprising elevating at least the small bowel, liver, spleen and stomach out of the pelvis.

6. A method of claim 1 comprising suturing said material around the peritoneal cavity.

7. A method of claim 1 comprising stapling said material around the peritoneal cavity.

8. A method of using a knitted surgical material in a warm-blooded mammal, said material comprising a plurality of filaments, each filament manufactured from a polymer having a glycolic acid ester linkage, said filaments bundled or twisted into a yarn, and said yarn knitted into said material, the method comprising:
  opening of the abdomen of said mammal;
  elevating at least one pelvic organ essentially out of the true pelvis;
  placing the material beneath the organ or organs from the elevating step;
  attaching said material to the wall of the peritoneal cavity, thereby preventing said organ or organs from descending into said pelvis; and
  closing said abdomen.

9. A method of claim 8 wherein said knitted material is a mesh.

10. A method of claim 8 wherein said knitted material is a fabric.

11. A method of claim 9 or 10 wherein said polymer is a homopolymer.

12. A method of claim 9 or 10 wherein said polymer is a copolymer.

13. A method of claim 9 wherein said yarn is greater than about 60 denier and contains up to 4 plys, each ply having greater than about 25 filaments.

14. A method of claim 10 wherein said yarn is up to about 150 denier and contains up to about 75 filaments.

15. A method of claim 14 wherein said yarn is about 100 to 135 denier and contains about 40 to 75 filaments.

16. A method of claim 14 or 15 manufactured on a 48 gauge Raschel knitting machine wherein the stitch design is Front Bar: 1/0 0/1, and
Back Bar: 1/0 4/5.

17. A method of claim 16 wherein the weight of said fabric is about 4 to 10 oz./sq. yd.

18. A method of claim 17 wherein the quality of said fabric is about 10 to 20 inches per 480 courses.

19. A method of using a knitted surgical mesh in a warm-blooded mammal, said mesh comprising a plurality of filaments, each filament manufactured from a polymer having a glycolic acid ester linkage, said filaments bundled or twisted into a yarn, and said yarn knitted into a mesh, the method comprising:

opening the abdomen of said mammal;

elevating at least the small bowel essentially out of the true pelvis;

placing said mesh adjacent to the intra-abdominal wall and beneath at least said bowel from the elevating step;

suturing said mesh to said intra-abdominal wall, thereby preventing at least said bowel from descending into said pelvis; and closing said abdomen.

* * * * *